United States Patent [19]
Ouchi

[11] Patent Number: 5,871,444
[45] Date of Patent: Feb. 16, 1999

[54] ELECTRODE CATHETER

[75] Inventor: Teruhiko Ouchi, Tokyo, Japan

[73] Assignee: Terumo Kabushiki Kaisha, Tokyo, Japan

[21] Appl. No.: 826,799

[22] Filed: Mar. 25, 1997

[30] Foreign Application Priority Data

Mar. 25, 1996 [JP] Japan .................................. 8-067653

[51] Int. Cl.$^6$ ...................................................... A61B 5/02
[52] U.S. Cl. ............................................................ 600/374
[58] Field of Search .................................. 607/122, 123, 607/124; 600/374, 381, 377

[56] References Cited

U.S. PATENT DOCUMENTS

| | | |
|---|---|---|
| 4,890,623 | 1/1990 | Cook et al. . |
| 4,945,912 | 8/1990 | Langberg ................................. 600/374 |
| 5,524,619 | 6/1996 | Ouchi et al. . |
| 5,531,719 | 7/1996 | Takahashi . |
| 5,569,200 | 10/1996 | Umeno et al. . |

FOREIGN PATENT DOCUMENTS

| | | |
|---|---|---|
| 6-319803 | 11/1994 | Japan . |
| 6-335460 | 12/1994 | Japan . |
| 94/21170 | 9/1994 | WIPO . |
| 95/10318 | 4/1995 | WIPO . |

*Primary Examiner*—Scott M. Getzow
*Attorney, Agent, or Firm*—Burns, Doane, Swecker & Mathis, LLP

[57] ABSTRACT

An electrode catheter includes a metal inner tube with distal and proximal ends and an outer tube formed of a synthetic resin so as to cover the outside surface of the inner tube. The inner tube has a helical slit formed from the distal end to a predetermined position, and one or more insulated wires are laid inside the inner tube from the proximal end to the distal end portion. One or more electrodes are disposed on the outer tube, with the wires extending out of the inner tube through the slit and connected to the electrodes. This electrode catheter possesses high pushability and torque-transmission capability along with a high flexibility and kink resistance, and can be easily inserted into a desired position of complexly branched thin blood vessels without kink or breakage of the wires caused by collapse of the lumen.

19 Claims, 3 Drawing Sheets

ELECTRODE CATHETER

BACKGROUND OF THE INVENTION

This invention relates to an electrode catheter which is inserted into the body of a patient for an electrophysiological examination, especially to an electrode catheter for use in the electrophysiological examinations made prior to the therapies for tachycardiac arrhythmia such as WPW (Wolff-Perkinson-White) syndrome or paroxysmal supraventricular tachycardia.

The electrophysiological examination made prior to the therapies for tachycardiac arrhythmia is conventionally performed by using a plurality of electrode catheters whose structure is such that one or two to ten electrodes are secured to the outside surface of the distal end portion, and the lead wires of the electrodes are extended through the inside of the hollow catheter to the proximal end for connection to a measuring apparatus. In the electrophysiological examination for bypass pathway-caused arrhythmia such as WPW syndrome, the bypass pathway which exists in the annulus of cardiac valves must be located- Since a thick coronary sinus runs in the annulus of mitral valve, measurements in the left heart portion can be performed relatively easily by inserting the multi-electrode catheter into the coronary sinus. However, there is no thick vein running in the annulus of tricuspid valve in the right heart portion. The right coronary artery running in this area is thin, and hence it is difficult to insert the conventional multi-electrode catheter into the right coronary artery. If the catheter could be inserted into the right coronary artery, there is a danger of causing acute myocardial infraction by obstructing the blood flow. For this reason, measurements in the annulus of tricuspid valve is performed by inserting an electrode catheter with an electrode at the tip into the right ventricle and moving the measuring position one point after another, resulting in a very cumbersome examination which takes a few hours.

Since the conventional examination is performed by using electrode catheters equipped with a small number of electrodes as described above, it takes a long time to locate the bypass pathway accurately. On the other hand, electrodes must be disposed at large intervals in order to measure over a wide area in a short time by a catheter with a small number of electrodes. It is difficult to locate the bypass pathway accurately by such a catheter with a small number of electrodes disposed at large intervals. Further, it is also difficult to increase the number of electrodes of the conventional electrode catheter in order to solve this problem. If the number of electrodes is increased, the number of signal transmitting wires must also be increased, resulting in a larger outside diameter of the catheter which makes examination of the right heart portion difficult.

An electrode probe to solve the above problem was proposed by the same inventors as of this application in Japanese Patent Application Laid-Open No. 335460/1994.The electrode probe has a plurality of electrodes which are formed by winding 12 wires for signal transmission on a PTCA guide wire made of Ni-Ti alloy and removing the insulating coating of the wires at the distal end portion of the winding.

This conventional electrode probe (electrode catheter) is relatively easy to insert into normal blood vessels. However, when there are lesions such as aneurysm and arteriovenous teratoid tumor in blood vessels, an electrode catheter must be inserted to an intended position by way of complexly branched thin blood vessels. To be easy to insert into thin blood vessels, an electrode catheter must have a high pushability which faithfully transmits a move in the axial direction applied to the proximal end portion to the distal end, a high torque transmitting ability which faithfully transmits a turn around the axis applied to the proximal end portion up to the distal end, and a high kink-resistance which prevents the catheter from collapsing at a bend in a blood vesseL However, the conventional electrode probe does not have sufficiently high pushability and torque transmitting ability because of the insufficient rigidity of the center wire which is made thin, though it has a high kink-resistance.

In addition, to lay the wires inside the catheter tube, a process which forms holes in the wall of the catheter tube, passes the wires through the holes from the inside to the outside of the catheter tube, and connects the wires to their corresponding electrodes is needed. This process can be applied to conventional electrode catheters whose inner tube diameter is equal to or greater than 2 mm and whose have up to three electrodes, though the working is difficult. However, for an electrode catheter whose inner tube diameter is 1.5 to 1.0 mm or smaller and whose has three electrodes, as thin as a guide wire, it is very difficult to form holes in the wall of the tube and to pass the wires through the thus-formed holes.

Further, if the outside diameter of a conventional electrode catheter is reduced, the diameter of the inner tube also becomes smaller. When the outside diameter is 1.0 mm, for example, the inside diameter becomes 0.6 mm since the wall thickness of about 0.2 mm is required to be usable as a catheter If the diameter of the wires used is 0.1 mm and 20 wires are laid inside the catheter, the lumen of the catheter is almost fully filled with the wires. When a bending stress is applied to this catheter, the catheter bends and exerts a stress on the lead wires which almost fully filling the lumen. The catheter collapses when an excessive bending stress is applied, exerting a greater stress on the wires. Since the wires almost fully filling the lumen of the catheter, deformation of the catheter exerts a stress on the wires, and the wires can break in the worst case.

The strength of the catheter decreases to provide the plural holes (especially, above four electrodes) to pass the wires to a catheter. The catheter may be broken at a part of the catheter provided many holes. This invention has been made in consideration of the above conventional electrode catheters. The object of this invention is to provide an electrode catheter whose number of electrodes can be increased without increase of the diameter, the problem with the conventional electrode catheter, and which has a high torque transmission capability, flexibility, and kink-resistance.

SUMMARY OF THE INVENTION

The electrode catheter of this invention comprises a metal inner tube with distal and proximal ends and an outer tube. Formed of a synthetic resin so as to cover the outside surface of the inner tube, and is characterized in that the inner tube has a helical slit formed in the portion of a predetermined length from the distal end, that at least one insulated wire is laid inside the inner tube from the proximal end to the distal end portion, that at least one electrode is secured to the outer tube, and that the wire is passed through the slit out of the inner tube and connected to the electrode.

DETAILED DESCRIPTION OF THE PREFERRED EMBODIMENTS

An embodiment of this invention is described below in detail with reference to the accompanying drawings.

Figure 1:
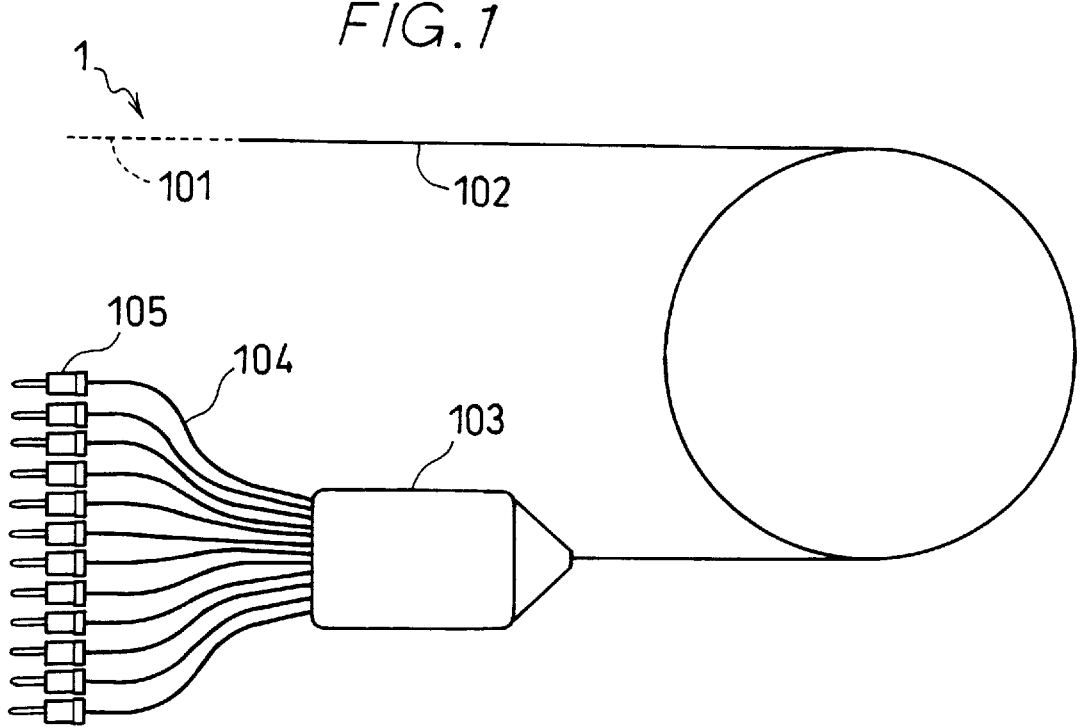
FIG. 1 is a perspective view of an embodiment of the electrode catheter of this invention.
Figure 2:
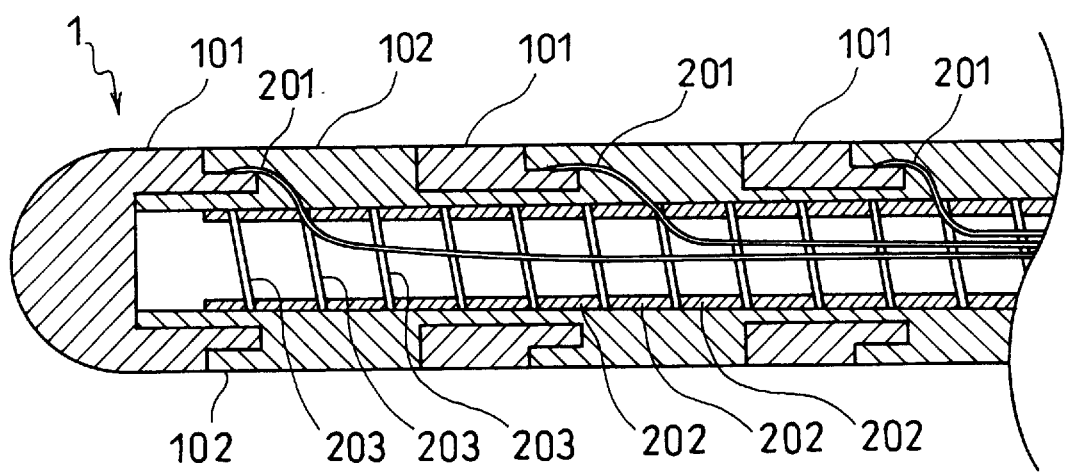
FIG. 2 is an enlarged sectional view of the distal end portion of the embodiment of the electrode catheter of this invention.
Figure 3:
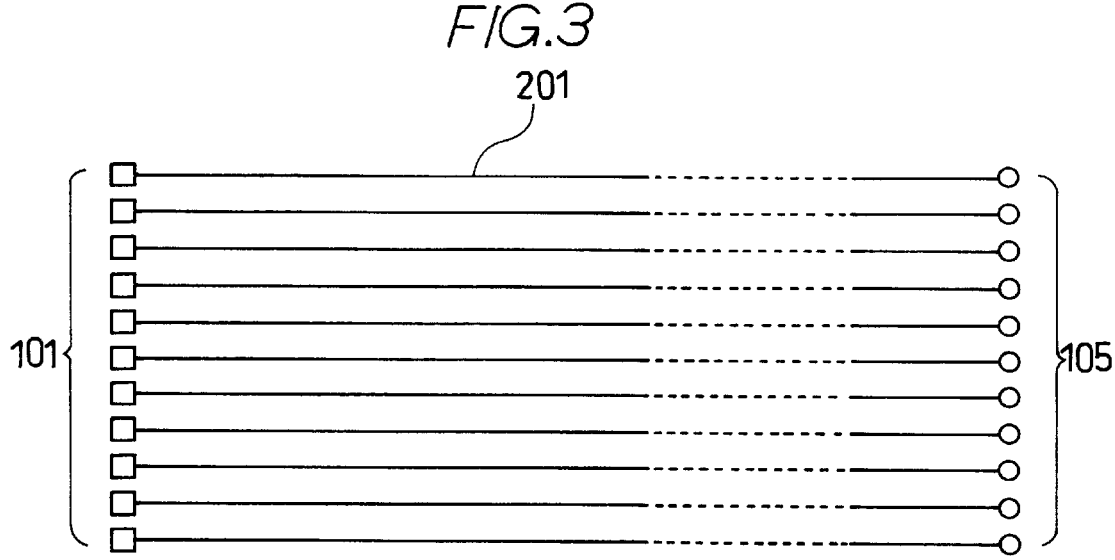
FIG. 3 is an equivalent circuit diagram of the embodiment of the electrode catheter of this invention.

FIG. 1 is a perspective view of an embodiment of the electrode catheter of this invention. FIG. 2 is an enlarged sectional view of the distal end portion of the electrode catheter shown in FIG. 1 which shows the structure of the inner tube, outer tube, and electrodes. FIG. 3 is an equivalent circuit diagram which shows the connection between the electrodes 101 at the distal end portion and the connectors 105 for taking the signals out of the catheter.

An electrode catheter 1 comprises a metal inner tube 202 with distal and proximal ends and an outer tube 102 formed of a synthetic resin so as to cover the outside surface of said inner tube 202. The inner tube 202 has a helical slit 203 formed from the distal end to a predetermined position, that one or more insulated wires 201 are laid inside the inner tube 202 from the proximal end to the distal end portion, that one or more electrodes 101 are disposed on the outer tube, and that the wires 201 are brought out of said inner tube 202 through said slit 203 and connected to the electrodes 101.

As shown in FIGS. 1 to 3, the electrode catheter 1 of this invention has a plurality of electrodes 101 disposed at the distal end portion and lead wires connected to the individual electrodes and laid inside the tubular body. The electrodes 101 are inserted into the cavity of the heart and put into contact with the cardiac muscle to measure the action potentials of the cardiac muscles. These electrodes 101 are connected to the connectors 105 one to one by means of the lead wires 201, as shown in FIG. 3. The signal from each connector is then amplified by a body signal amplifier not shown in the Figures. Finally, the action potentials are displayed on a CRT or recorded by a recorder.

Each lead wire 201 is passed through a helical slit 203 formed in the metal inner tube 202 out of the inner tube and electrically connected to the corresponding electrode 101 by welding or bonding. The outer tube 201 is formed of an insulating material, for example, a synthetic resin such as polyurethane, to prevent the electrodes 101 from coming into contact with the metal inner tube.

A flexible electrode catheter with a bending resistance gradually decreasing toward the distal end can be obtained by forming the slit 203 in such a manner that the pitch of the helix becomes smaller toward the distal end or forming the slit 203 in such a manner that the width of the slit 203 becomes wider smaller toward the distal end. It is also possible to provide the proximal end of the electrode catheter with a high pushability and the distal end portion with a high flexibility which allows the distal end portion to follow complicate meanders of blood vessels, by forming the slit only in the distal end portion. Thus it is possible to determine the features of the catheter as desired by the manner the slit is formed. The width of the slit 203 is preferably within the range of about $\frac{1}{10}$ to $\frac{1}{4}$ of the outside diameter of the inner tube 202, but must not be within this range since the width of the slit is determined taking the diameter of the outer tube 102 and other factors into consideration. Basically, the width of the slit is preferably within the range of about 0.01 to 1.5 mm, more preferably 0.01 to 1 mm. The width of the middle portion may be an intermediate value between the width of both end portions of the inner tube or may become gradually larger from the width of the proximal end portion to that of the distal end portion of the inner tube.

The pitch of the slit is preferably within the range of about 0.3 to 3 mm at the distal-side end portion of the slit and 5 to 10 mm at the proximal-side end portion. In the middle part between the distal-side and proximal-side end portions, the slit may have a uniform pitch intermediate between those at the distal-side and proximal-side end portions or a gradually changing pitch from the pitch at one end portion to that at the other end portion. The length of the portion in which the slit is formed is preferably within the range of about 100 to 1000 mm, more preferably 150 to 500 mm. If the length of that portion is within this range, the catheter has a sufficient flexibility not to break.

For the material for the inner tube 202, a metal such as iron, tungsten, or copper; an alloy containing any of these metals such as austenitic alloy stainless steel (SUS304, SUS316, or SUS32, for example), maraging stainless steel, Cu-Zn alloy, or Cu-Sn alloy; or a super high-resilience alloy (shape-memory alloy) represented by Ni-Ti alloy can be used, An austenitic alloy stainless steel is preferable.

The Slit is formed in the metal or alloy tube by any of conventional techniques including laser machining (e.g., YAG laser), electric discharge machining, chemical etching, machining, and combinations thereof. Further, the metal tube (inner tube) formed with the slit is preferably subjected to the chamfering process which removes edges and burrs of the tube. This chamfering is performed, for example, by shotblast using a fine hard abrasive. The inner tube of the catheter has the slit having a rounding edge.

Although the inner tube shown in the Figure has a uniform thickness, the wall thickness of the inner tube may become gradually smaller from an appropriately determined position toward the distal end. If the wall thickness of the inner tub 202 is made so as to become gradually smaller toward the distal end, the rigidity of the inner tube also decreases gradually toward the distal end. As the result, the force with which the distal end of the catheter presses against the wall of a blood vessel can be reduced without a discontinuous change in rigidity near the distal end. This increases the kink resistance of the catheter.

For the lead wires 201, wire whose core is made of a low-electric resistance metal such as gold, silver, or copper and coated with an insulating layer (polyurethane, enamel, or fluororesin, for example) is used. Although the diameter of the wires is determined according to the outside diameter of the electrode catheter, it is preferably within the range of 20 to 30 $\mu$m in diameter of the core and within the range of 30 to 50 $\mu$m in outside diameter including the insulating layer. By use of different colors for the insulating layers of the wires, miswiring in the manufacturing process can be prevented.

Although there is no particular limit on the dimensions of the electrode catheter of this embodiment, the electrode catheter for measuring the action potentials of the heart is preferably within the range of about 50 to 400 cm, especially about 70 to 150 cm in overall length of the catheter portion, and preferably within the range of about 0.5 to 7 mm, especially about 0.7 to 6 mm in outside diameter of the catheter portion, for example.

The wall thickness of the outer tube 102 of the catheter portion is preferably within the range of about 5 to 300 μm, more preferably about 10 to 200 μm. The wall thickness of the outer tube 102 of the electrode portion is preferably within the range of about 5 to 300 μm, more preferably about 5 to 50 μm. The wall thickness of the inner tube 202 of the electrode portion is preferably within the range of about 50 to 200 μm, more preferably about 50 to 150 μm.

The outer tube 102 is preferably formed of a material with a comparatively large rigidity. For the material for the outer tube 102, a thermoplasticlastic resin [polyolfin (polyethylene, polypropylene, or ethylene-propylene copolymer, etc.), polyolefin elastomer (polyethylene elastomer, polypropylene elastomer, or ethylene-propylene copolymer elastomer, etc.), poly(vinyl chloride), ethylene-vinyl acetate copolymer, polyamide elastomer, polyurethane, fluororesin, etc. or silicone rubber can be used. Of these resins, polyethylene, polyamide elastomer, or polyurethane is most preferable. For the material for the outer tube, a material with a low electric conductivity or a substantially insulating material is preferable.

An X-ray contrast medium in fine power, made of a metal such as Ba, W or Bi or an alloy of any of them, may he mixed in the synthetic resin for the outer tube 102. By thus dispersing an X-ray contrast medium in the outer tube, it is made easier to view the position of the entire catheter which is being inserted into blood vessels. For this purpose, an X-ray contrast medium with a low electric conductivity is preferable.

The outside surface of the outer tube 102 may be coated with a biologically compatible synthetic resin, particularly a synthetic resin with an antithrombogenic property-For the anti-thrombogenic substance, polyhydroxymethacrylate or a copolymer of hydroxyethylmethacrylate and styrene HEMA-St-HEMA block copolymer, for example) is preferable.

The outside surface of the outer tube 203 is preferably treated so as to present a high lubricity when it is in contact with a body liquid such as blood. For this treatment, coating the outside surface of the outer tube with a hydrophilic polymer, such as poly(2-hydroxyethylmethacrylate), polyhydroxyethylacrylatehydroxypropylcellulose, methylvinylether-maleic anhydride copolymer, polyethylene glycol, polyacrylamide, or polyvinylpyrrolidone can be used. The thickness of the lubricating layer of a hydrophilic polymer is preferably within the range of about 0.1 to 100 μm, especially about 1 to 30 μm, though there is no particular limit Although the resin material of the outer tube 102 may fill the slit 203 of the inner tube 202, it is preferable that the resin material does not flow into the slit 203, leaving the slit 203 empty. If the resin material of the outer tube 102 is not in the slit 203, deformation of the inner tube 202 is not hindered by the resin in the slit 203.

The flexural elasticity (ASTM D-790, 23° C.) of the outer tube 102, especially of its distal end portion, is preferably within the range of 5 to 1500 kg/cm$^2$, more preferably 10 to 800 kg/cm$^2$. If the flexural elasticity of the outer tube is smaller than 5 kg/cm$^2$, a pushing force or torque applied to the proximal end portion of the catheter is not faithfully transmitted to the electrode portion at the distal end. Further, the difference of the rigidity between the catheter portion and the electrode portion becomes large to considerably decrease the kink resistance at the boundary region. If the flexural elasticity of the outer tube is greater than 1500 kg/cm$^2$, on the other hand, the guide wire-following capability of the catheter becomes low to give greater stimuli to the inside wall of blood vessels.

The width of the electrodes 102 is preferably within the range of 0.1 to 5 mm, especially 0.5 to 2 mm. The distance between adjacent electrodes is preferably within the range of 0.1 to 20 mm, especially 0.5 to 5 mm.

It is desirable for the catheter of the invention to be equipped with four electrodes at least. Especially, a pair is comprised of two electrodes, it is desirable to be equipped with at least two pairs of the electrodes to the catheter of the invention.

Figure 4:
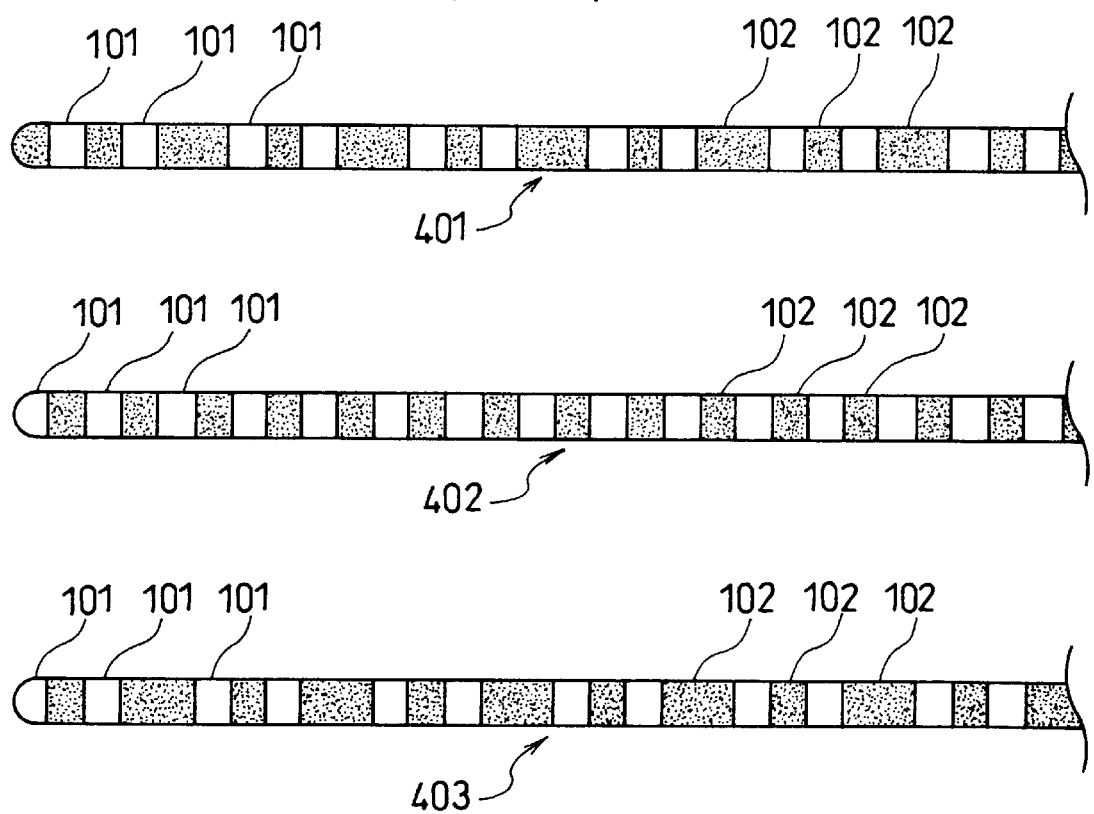
FIG. 4 shows variations of the electrode arrangement of the embodiment of the electrode catheter of this invention

FIG. 4 shows variations of the electrode arrangement. Unfilled parts represent electrodes. In electrode arrangement 401, two electrodes are combined into a pair, and pairs of two electrodes are disposed at the same intervals, with no electrode disposed at the tip. In electrode arrangement 402, all electrodes are disposed at the same intervals from the tip. In electrode arrangement 403, two electrodes are combined into a pair, and pairs of two electrodes are disposed at the same intervals, in the same manner as in electrode arrangement 401, except that an electrode is disposed at the tip. These electrode arrangements must not be exactly as shown in the Figure. The electrodes may be disposed at different intervals, for example. The number of electrodes is within the range of 1 to 40, preferably 2 to 24, though the maximum number of electrodes that can be attached to the catheter is limited by the outside diameter of the electrodes catheter.

Figure 5:
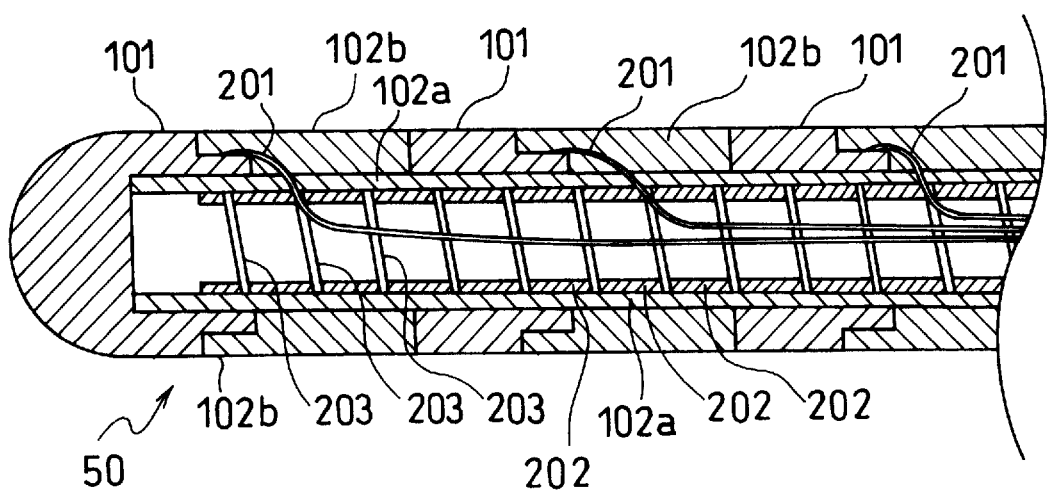
FIG. 5 is an enlarged sectional view of the distal end portion of the another embodiment of the electrode catheter of this invention.

For the material for forming the electrodes, metals with a high-electric conductivity (gold, platinum, silver, copper, etc.) and their alloys can be used. Platinum or stainless steel (SUS-304, SUS-3126, etc.) is preferable. The shape of electrodes is preferably a circular band as shown in FIG. 2. The electrodes are secured to the catheter so that they do not come into contact with the inner tube. Specifically, the electrodes are secured on the insulating layer formed of the same material as for the outer tube over the surface of the inner tube. Then, the outer tube is formed in such a manner that the outside surface of the electrodes is exposed and continuous with the outside surface of the outer tube substantially without a step. The insulating layer to cover the surface of the inner tube with may be formed of a material different from that for the outer tube as shown in FIG. 5. This catheter 50 has a three-layer structure. The outer tube of this catheter has an insulating layer 102a and a outer layer 102b. The insulating layer 102a covers the surface of the inner tube 202. The electrodes 101 are secured to the catheter so that they do not come into contact with the inner tube 202. The electrodes 101 are secured on the insulating layer 102a. The outer layer 102b cover the surface of the insulating layer 102a of a part where the electrodes are not secured. Then, the outer layer 102b is formed in such a manner that the outside surface of the electrodes 101 is exposed and continuous with the outside surface of the outer layer ( outer tube ) substantially without a step. The insulating layer 102a to cover the surface of the inner tube with may be formed of a material same or different from that for the outer tube.

The electrode catheter of this invention has been described on the basis of the embodiments shown in Figures, but this invention is not limited to those described structures. For example, the distal end portion of the inner tube 202 in which the slit is formed may be made of a material with a flexibility higher than that of the material for the other portion of the inner tube 202 in order to make the distal end portion of the inner tube more flexible than the other part. Further, the inside surface of the inner tube 202 may be coated with the same synthetic resin as used to form the outer tube 102.

By the above described structure, the electrode catheter of this invention has a mechanical property improved in pushability, torque transmission, and kink-resistance, and can be inserted into a desired position of complexly branched thin blood vessels when a patient has lesions in blood vessels.

Since a helical slit is formed in the distal end portion of the inner tube, the ends of the signal wires passed through the inner tube can be taken out of the inner tube though the slit all at once, and hence it becomes easier to pick up a needed wire, when the catheter is provided with a plurality of electrodes.

Further, if an excessive stress is applied to the portion of the catheter with the slit formed therein, the stress can be evenly dispersed without causing collapse of the lumen. Therefore, breakage of the wires laid in the lumen caused by collapse of the lumen can be prevented.

By this invention, as described above, an improved electrode catheter can be made by forming a helical slit in a metal inner tube, passing a plurality of lead wires through a metal inner tube, take the lead wires out of the inner tube through the slot, and connecting the lead wires brought out of the inner tube to their corresponding electrodes disposed on the distal end portion. Since a bending stress applied to the catheter body is dispersed by the slit, the catheter has a high kink resistance. The flexibility of the catheter can be changed by changing the width and pitch of the slit or the length of the portion where the slit is formed. Therefore, a small-diameter electrode catheter that has a high pushablity and torque-transmission capability which faithfully transmit pushing force and torque applied to the proximal end portion to the distal end portion, along with a high flexibility and kink resistance which allow the electrode catheter to bend following blood vessels even at their curved or bent portions without collapse of the lumen and can be easily inserted into a desired position of complexly branched thin blood vessels without kink or breakage of the wires caused by collapse of the lumen can be obtained.

I claim:

1. An electrode catheter comprising:
    a metal inner tube with distal and proximal ends, said inner tube having an outside surface and being provided with a helical slit formed in a portion of the inner tube over a predetermined length from the distal end;
    an outer tube formed of a synthetic resin and covering the outside surface of said inner tube;
    at least one electrode secured to the outer tube adjacent a distal portion of said outer tube and located at a position wherein said helical slit is located; and
    at least one insulated wire extending inside said inner tube from the proximal end to a distal end portion of the inner tube, said at least one insulated wire extending out of said inner tube through said slit and being connected to said electrode.

2. The electrode catheter of claim 1, wherein said helical slit possesses a pitch that is smaller at distal side end of said inner tube than at a proximal side end of said inner tube.

3. The electrode catheter of claim 1, wherein said helical slit possesses a width that is larger at distal side end of said inner tube than at a proximal side end of said inner tube.

4. The electrode catheter of claim 1, wherein said inner tube is made of iron, tungsten, copper, or an alloy of iron tungsten or copper.

5. The electrode catheter of claim 1, wherein said inner tube possesses a wall thickness that is 1.5 mm or smaller.

6. The electrode catheter of claim 1, including a pair electrodes secured to said outer tube and wires each connected to one of said electrodes, each wire being located inside said inner tube and extending from adjacent the proximal end to the distal end portion of the inner tube, with each wire extending through said slit.

7. The electrode catheter of claim 6, including at least two pairs of electrodes.

8. The electrode catheter of claim 1, including at least four electrodes secured to said outer tube and a plurality of wires each connected to one of said electrodes and extending within said inner tube from adjacent the proximal end and through said slit.

9. The electrode catheter of claim 1, including a plurality of electrodes secured to said outer tube and a plurality of wires each connected to one of said electrodes, said wires being brought into said inner tube through said slit, and extending through said inner tube to the proximal end.

10. The electrode catheter of claim 1, wherein the electrodes and the outer tube possess outside surfaces, the outside surface of said at least one electrode being continuous with the outside surface of said outer tube substantially without a step.

11. The electrode catheter of claim 1, wherein said outer tube has an insulating layer and an outer layer, the insulating layer covering an outer surface of the inner tube, the at least one electrode being secured on the insulating layer, the outer layer covering a part of a surface of the insulating layer where the at least one electrode is not secured, and the outer layer being formed in such a manner that an outside surface of the at least one electrode is exposed and is continuous with an outside surface of the outer layer substantially without a step.

12. An electrode catheter comprising:
    an outer tube having a distal portion;
    an inner tube positioned within said outer tube, said inner tube having a distal end and a proximal end, said inner tube being provided with a helical slit formed in at least a portion of the inner tube located adjacent the distal end of the inner tube;
    at least one electrode secured to the distal portion of said outer tube and located at a position at which said helical slit is located; and
    at least one insulated wire located within said inner tube, said at least one insulated wire extending out of said inner tube through said slit and being connected to said at least one electrode.

13. The electrode catheter of claim 12, wherein said helical slit possesses a pitch that is smaller at a distal side end of said inner tube than at a proximal side end of said inner tube.

14. The electrode catheter of claim 12, wherein said helical slit possesses a width that is larger at a distal side end of said inner tube than at a proximal side end of said inner tube.

15. The electrode catheter of claim 12, wherein said inner tube is made of iron, tungsten, copper, or an alloy of iron, tungsten or copper.

16. The electrode catheter of claim 12, wherein said inner tube possesses a wall thickness that is 1.5 mm or smaller.

17. The electrode catheter of claim 12, including a plurality of electrodes secured to said outer tube and a plurality of wires each connected to one of said electrodes, said wires being located within said inner tube and extending out through said slit.

18. The electrode catheter of claim 12, wherein the electrodes and the outer tube possess outside surfaces, the outside surface of said at least one electrode being continuous with the outside surface of said outer tube substantially without a step.

19. The electrode catheter of claim 12, wherein said outer tube has an insulating layer and an outer layer, the insulating layer covering an outer surface of the inner tube, the at least one electrode being secured on the insulating layer, the outer layer covering a part of a surface of the insulating layer where the at least one electrode is not secured, and the outer layer being formed in such a manner that an outside surface of the at least one electrode is exposed and is continuous with an outside surface of the outer layer substantially without a step.

* * * * *

UNITED STATES PATENT AND TRADEMARK OFFICE
CERTIFICATE OF CORRECTION

PATENT NO. : 5,871,444
DATED : February 16, 1999
INVENTOR(S) : Teruhiko OUCHI

It is certified that error appears in the above-indentified patent and that said Letters Patent is hereby corrected as shown below:

In column 2, lines 55 and 56, delete "tube. Formed" and insert --tube formed--.
In column 5, line 19, insert --]-- after "etc.".
In column 6, line 44, change "a outer" to --an outer--.
In Claim 2, line 2, insert --a-- between "at" and "distal".
In Claim 3, line 2, insert --a-- between "at" and distal".
In Claim 6, line 2, insert --of-- before "electrodes".

Signed and Sealed this

Fourteenth Day of September, 1999

Attest:

Q. TODD DICKINSON

*Attesting Officer*   *Acting Commissioner of Patents and Trademarks*